United States Patent [19]
Sheahon

[11] Patent Number: 5,476,104
[45] Date of Patent: Dec. 19, 1995

[54] CERVICAL AND ENDOMETRIAL BIOPSY INSTRUMENT

[76] Inventor: John A. Sheahon, U-2, Rte. 4, Lake Lotawana, Mo. 64063

[21] Appl. No.: 283,565

[22] Filed: Aug. 1, 1994

[51] Int. Cl.$^6$ ................................................. A61B 10/00
[52] U.S. Cl. ................................................................. 128/757
[58] Field of Search ............................... 128/749, 751, 128/756–759; 604/1

[56]     References Cited

U.S. PATENT DOCUMENTS

| | | |
|---|---|---|
| D. 210,757 | 4/1968 | Michel . |
| 584,407 | 6/1897 | Saint Cyr, Jr. . |
| 626,625 | 6/1899 | May . |
| 667,726 | 2/1901 | McDade . |
| 865,571 | 9/1907 | Currey . |
| 2,955,591 | 10/1960 | MacLean . |
| 2,955,592 | 10/1960 | MacLean . |
| 3,592,186 | 7/1971 | Oster . |
| 3,613,664 | 10/1971 | Willson . |
| 3,796,211 | 3/1974 | Kohl . |
| 4,027,658 | 6/1977 | Marshall ............................ 128/757 |
| 4,054,127 | 10/1977 | Milan et al. . |
| 4,243,049 | 1/1981 | Goodale et al. . |
| 4,361,948 | 12/1982 | Omata . |
| 4,396,022 | 8/1983 | Marx . |
| 4,627,444 | 12/1986 | Brooker . |
| 4,961,430 | 10/1990 | Sheahon . |
| 5,092,345 | 3/1992 | Sakita ............................... 128/757 |

OTHER PUBLICATIONS

"Transcervical Balloon Tuboplasty", Tur–Kaspa and Gleicher, The Female Patient/vol. 18, Feb. 1993.
"Suction Curettage with a Tissue Trap Compared with Sharp Curettage for Tissue Sampling", Gimpelson and Hill, The Journal of Reproductive Medicine, Inc., Feb. 10, 1993.

*Primary Examiner*—Max Hinderburg
*Attorney, Agent, or Firm*—Chase & Yakimo

[57]            ABSTRACT

A biopsy instrument for obtaining a tissue sample from a body cavity such as the endometrial tissue forming the uterine cavity or from the cervix. The instrument comprises a first generally rigid guide housing for insertion into the cavity. An elongated, flexible shaft is slidable therethrough and has spaced from its distal end a curved portion for collecting a tissue specimen thereon. The curved portion includes a set of scraping tabs and a set of collecting tabs spaced apart around the circumference of the curved portion and extending alternately outwardly therefrom. After the shaft is extended from within the housing and rotated in a first direction, the scraping tabs scrape tissue free from the endometrial surface. Upon rotating the shaft in a second opposite direction, the collecting tabs collect the free floating tissue. When the shaft is retracted within the housing, the instrument is removed from within the body cavity, and a tissue sample is available for testing.

11 Claims, 2 Drawing Sheets

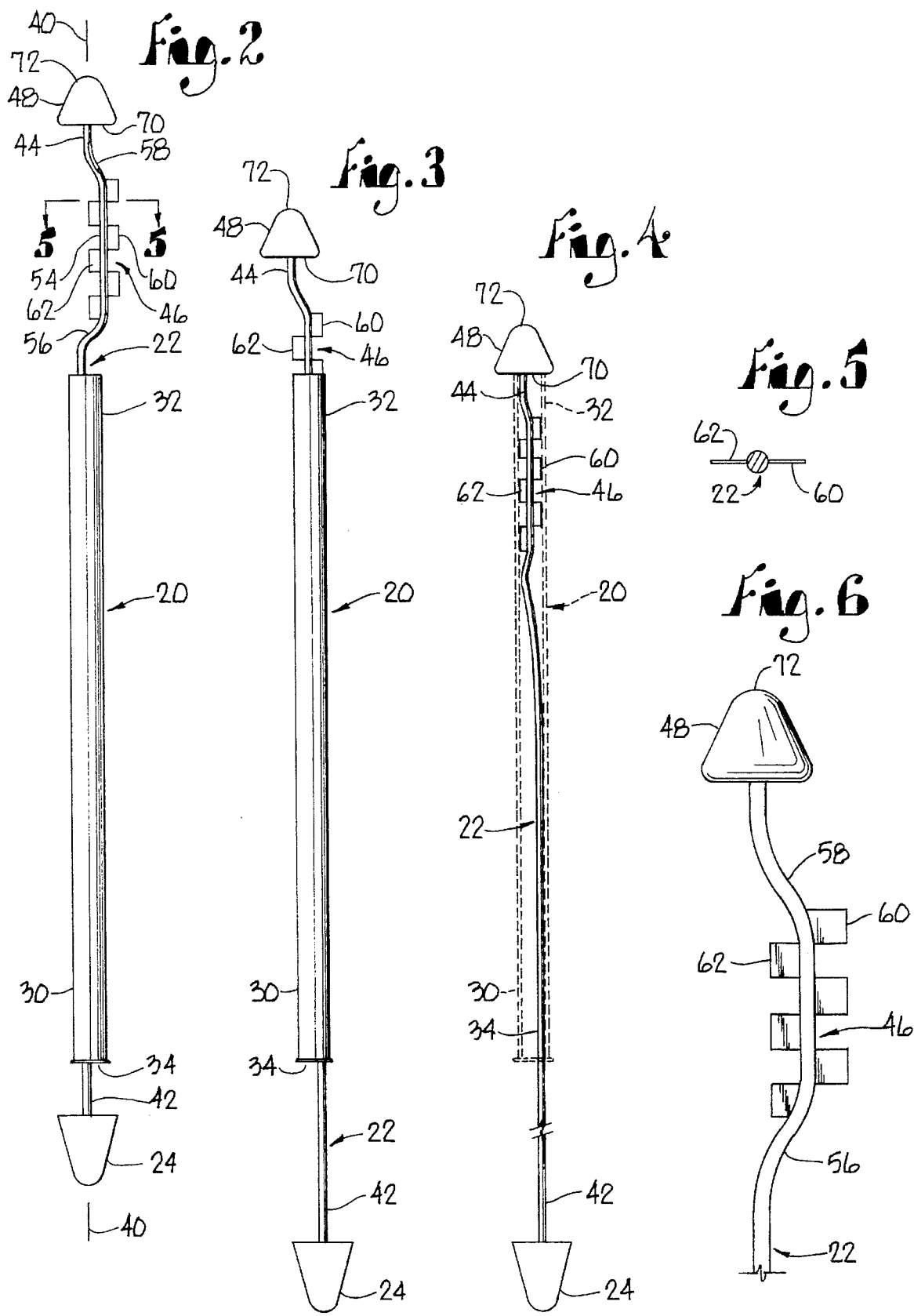

CERVICAL AND ENDOMETRIAL BIOPSY INSTRUMENT

BACKGROUND OF THE INVENTION

This invention relates to an instrument for extracting a biopsy specimen from a body cavity, and more particularly, to an instrument for providing a cervical or endometrial tissue biopsy.

Various instruments in the prior art are known for extracting a biopsy section. One such instrument is my cervical biopsy instrument is shown in my patent, U.S. Pat. No. 4,961,430, which is effective in obtaining a cervical biopsy.

However, an endometrial tissue evaluation requires tissue extraction from the uterine cavity. Due to the curvature of the surface forming the uterine cavity, the cutting tip of the biopsy instrument must be first manipulated by the physician through the cervical opening and then into contact with the endometrial tissue. Flexion of the instrument is best desired to allow the instrument to conform to the uterus shape and enhance tissue contact. Such a device endometrial sampling.

Although there are known devices which attempt to address this function, such devices have problems inherent in their structure. In some cases, as panoramic samples are to be taken about the uterus, the instrument must be repeatedly withdrawn and inserted for each sample. Such requirements can increase patient discomfort. Also, it is necessary to first insert the instrument through the cervical opening and then direct the flexible instrument toward the endometrial tissue. This manipulation of the device bears against the cervical opening which can increase patient discomfort.

In response thereto I have provided an endometrial biopsy instrument which is first easily positioned with the uterus and adjacent the desired endometrial tissue so as to obtain an endometrial tissue specimen or specimens about the panorama of the uterus with minimal discomfort, if any, to the patient.

My biopsy instrument generally comprises an elongated tubular housing having a flexible tubular shaft therein. The shaft has a flexible curved portion off-set from the axis of the shaft and displaced from the distal end of the shaft. This curved portion has a first and second set of tabs which are spaced apart and extend in opposed directions from the curved portion so that the tabs are not in alignment. The first set of tabs scrape the tissue surface when the shaft is extended from within the housing and rotated in a first direction. The second set of tabs collect the scraped tissue when the shaft is rotated in a second direction and retracted into the housing. The shaft may also have a tapered head portion forming a rounded tip at the distal end thereof which engages the distal end of the body cavity to limit the penetration of the shaft into the body cavity. Also, the head provides a pivot point which prevents the shaft from swinging in a wide arc during rotation. A stop member is coupled to the proximal end of the shaft for further preventing over-insertion of the shaft within the body cavity and thus, further prevents discomfort to the patient. Upon retraction of the shaft into the housing, the curved portion is urged into a storage configuration. Upon withdrawal of the biopsy instrument from the body cavity, the collected tissue is available for subsequent analysis.

It is therefore a general object of this invention to provide an endometrial and cervical biopsy instrument.

Another object of this invention is to provide an instrument, as aforesaid, which may be used with minimal discomfort, if any, to the patient.

A further object of this invention is to provide an instrument, as aforesaid, that conforms to the shape of the uterine cavity so as to enhance tissue contact while avoiding discomfort to the patient.

Still a further object of this invention is to provide an instrument, as aforesaid, which allows tissue samples to be easily taken about the panorama of the body or uterine cavity.

Another object of this invention is to provide an instrument, as aforesaid, which is easily inserted through the cervical opening and into the uterine cavity with little resistance or accompanying discomfort to the patient.

A further object of this invention is to provide an instrument, as aforesaid, which utilizes a first generally rigid guide housing and a second relatively flexible collection shaft to obtain a tissue sample.

A more particular object of this invention is to provide an instrument, as aforesaid, which uses scraping tabs and collecting tabs to enhance the collection of tissue samples about the panorama of the body or uterine cavity as the shaft is rotated.

A still further object of this invention is to provide an instrument, as aforesaid, which utilizes a flexible shaft having a first working configuration and a second storage configuration.

Another particular object of this invention is to provide an instrument, as aforesaid, which is intended for a one-time use so as to eliminate the transfer of infection between patients.

Other objects and advantages of this invention will become apparent from the following description taken in connection with the accompanying drawings, wherein is set forth by way of illustration and example, an embodiment of this invention.

BRIEF DESCRIPTION OF THE DRAWINGS

FIG. 2 is a front elevation view of the biopsy instrument of FIG. 1 showing the working end of the shaft in a curved configuration upon its extension from within the housing;

FIG. 3 is a front elevation view of the biopsy instrument of FIG. 1 showing the curved portion of the shaft partially retracted within the housing;

FIG. 4 is a front elevation view of the biopsy instrument of FIG. 1, as sectioned along the longitudinal center line, to show the storage configuration of the shaft within the housing;

FIG. 5 is a cross-sectional view of the biopsy instrument of FIG. 2 taken along line 5—5 showing the scraping and collecting tabs extending outwardly from the shaft on an enlarged scale;

FIG. 6 is a partial front elevation view of the working end of an alternate embodiment of the shaft, on an enlarged scale, wherein the curved portion has a more gradual slope than that of the curved portion of FIG. 2.

DESCRIPTION OF THE PREFERRED EMBODIMENT

Figure 1:
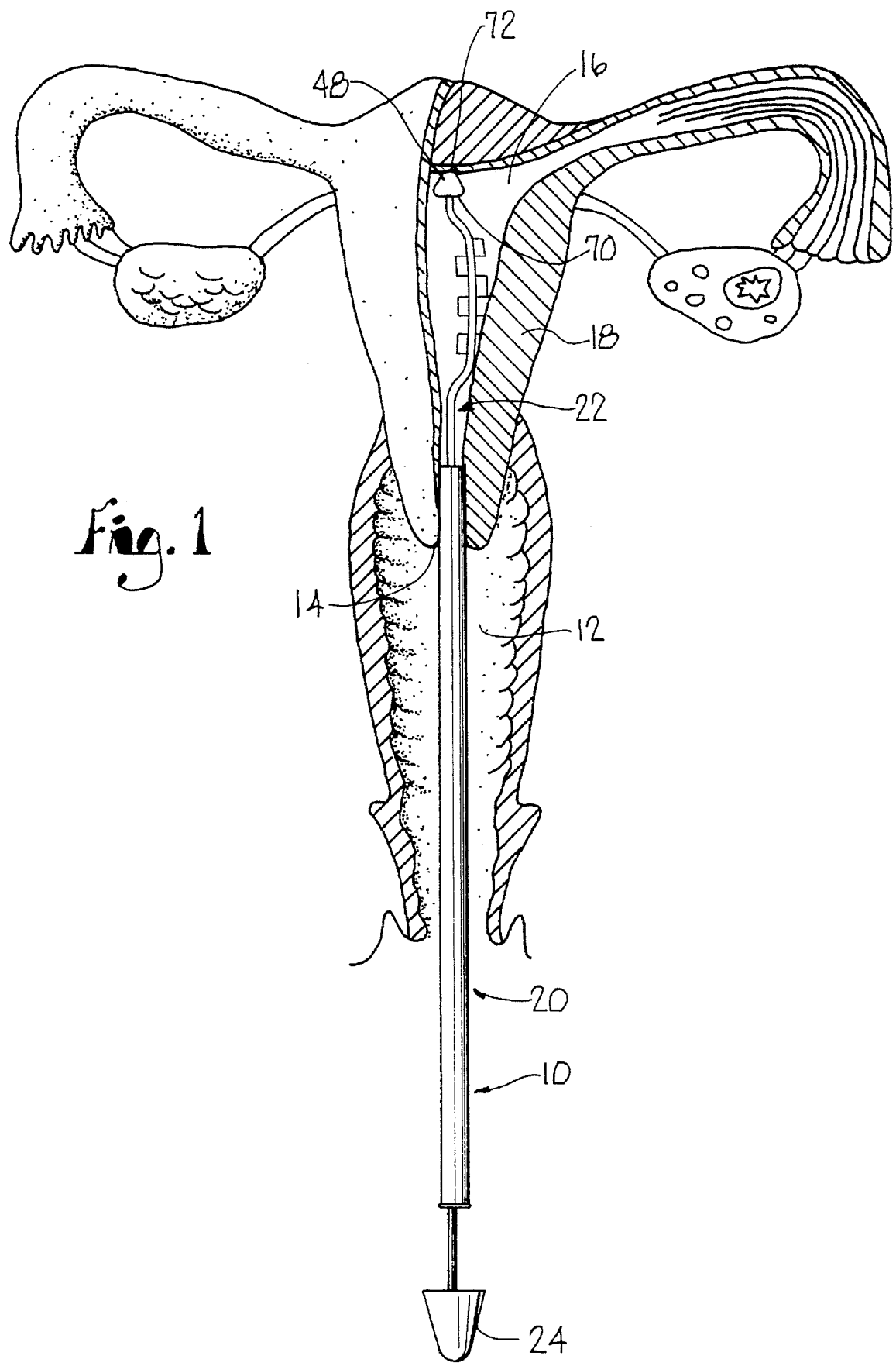
FIG. 1 is a diagrammatic view of the female internal reproductive organs and showing the biopsy instrument in position for collecting an endometrial tissue specimen.

Turning more particularly to the drawings, FIG. 1 shows the endometrial biopsy instrument 10 extending through the vaginal canal 12, the cervical opening 14 and into the uterine cavity 16. The biopsy instrument 10 includes tubular guide housing 20 and an elongated tubular shaft 22 which is slidable within guide housing 20. When shaft 22 is extended from within housing 20, as in FIG. 1, shaft 22 collects endometrial tissue samples from endometrial surface 18.

Guide housing 20 acts as a protective sheath for shaft 22. Housing 20 is elongated and tubular and preferably has a circular cross-section. It is also integrally formed and is preferably molded from rigid plastic. As seen in FIGS. 2–4, housing 20 has a proximal end 30 and a distal end 32 relative to the position of the physician and includes a through passageway 34 which extends the length of housing 20 from its proximal end 30 through its distal end 32.

Elongated shaft 22 is receivable within passageway 34 of housing 20 and is extendable and retractable therethrough as seen in FIGS. 2–4. Shaft 22 is composed of flexible, resilient plastic and is preferably integrally and unitarily formed having a circular cross-section with a diameter less than the diameter of passageway 34. Thus, shaft 22 is rotatable 360° in a first and second direction within passageway 34 of housing 20.

As seen in FIGS. 2–4, shaft 22, like housing 20, has a proximal end 42 and a distal working end 44 relative to the position of the physician. Shaft 22 also has a curved portion 46 displaced from or adjacent its distal end 44 and a tapered head portion 48 formed at its distal end 44.

Curved portion 46 is off-set from the central longitudinal axis 40 of the shaft 22 adjacent the distal end 44 of shaft 22 and has a main segment 54 which extends substantially parallel to the primary longitudinal axis 40. Preferably, curved portion 46 is longitudinally off-set from the primary axis 40 of shaft 22 about 4 millimeters and extends 1 inch to 1½ inches along the length of shaft 22. Curved portion 46 can be off-set either as shown in FIGS. 1–4 or as in FIG. 7. As in FIG. 7, the slope of shaft 22 is more gradual at the first end 56 of curved portion 46 than it is in FIGS. 1–4. The slope of second end 58 of curved portion 46 may also be reduced if desirable. If curved portion 46 is configured as in FIG. 7, it can be formed from more rigid plastic since the retraction of shaft 22 into housing 20 is easier and less flexion is necessary.

Curved portion 46 includes a first set of scraping tabs 60 and a second set of collecting tabs 62 which form two columns extending outwardly in opposed directions from the main segment 54 of curved portion 46 and parallel to longitudinal axis 40. Scraping tabs 60 and collecting tabs 62 are preferably spaced 180° apart around the circumference of curved portion 46 and extend alternately outwardly therefrom so that scraping tabs 60 are not in alignment with collecting tabs 62, as seen in FIGS. 2–5. In other words, scraping tabs 60 are off-set from collecting tabs 62. Additionally, scraping tabs 60 are themselves spaced apart from the next adjacent scraping tab 60, and likewise, collecting tabs 62 are spaced apart from the next adjacent collecting tab 62. Thus, scraping tabs 60 and collecting tabs 62 are interrupted and preferably do not form a continuous blade. Scraping tabs 60 and collecting tabs 62 are preferably rectangularly shaped and composed of rigid plastic.

Tapered head portion 48 is formed at the distal end 44 of shaft 22, spaced from curved portion 46 as seen in FIGS. 2–4. Head portion 48 has a first end 70 engageable with the distal end 32 of guide housing 20 when the shaft 22 is retracted within housing 20, as in FIG. 4. Thus, the diameter of first end 70 of head portion 48 must be greater than the diameter of passageway 34 and is preferably equal to the diameter of housing 20 so that biopsy instrument presents a continuous, smooth surface. Head portion 48 is shaped like a bullet and tapers inwardly to form a smooth, rounded tip at its second end 72 which is engageable with the wall of uterine cavity 16 when shaft 22 is extended, as in FIGS. 1 and 2.

Stop member 24 extends outwardly from the proximal end 42 of shaft 22 and is engageable with the proximal end 30 of housing 20 when shaft 22 is fully extended from within housing 20. Thus, the diameter of stop member 24 must be greater than the diameter of passageway 34. Preferably, stop member 24 is composed of rigid plastic and is fixedly coupled to the proximal end 42 of shaft 22.

Assembly and Operation

To assemble biopsy instrument 10 as seen in FIGS. 1–4, elongated shaft 22 is inserted into through passageway 34 of guide housing 20. Specifically, the proximal end 42 of shaft 22 is inserted through the distal end 32 of housing 20 into passageway 34. The first end 70 of tapered head portion 48 of shaft 22 ultimately engages the distal end 32 of housing 20, as seen in FIG. 4. As the shaft 22 is inserted through passageway 34, the curved portion 46 of shaft 22 resiliently flexes inwardly toward longitudinal axis 40 as in FIG. 4 so as to assume a storage configuration.

Stop member 24 is fixedly coupled to the proximal end 42 of shaft 22. Shaft 22 is then extendable and retractable from within housing 20 such that the tapered head portion 48 and stop member 24 slidably and adjustably couple the shaft 22 within housing 20.

In operation, biopsy instrument 10 is inserted into uterine cavity 16 as in FIG. 1 when an endometrial tissue sample is to be taken. The distal end 44 of shaft 22, or in other words tapered head portion 48, and distal end 32 of housing 20 are inserted through the vaginal canal 12 and the cervical opening 14 into the uterine cavity 16 as in FIG. 1. During insertion, tapered head portion 48 prevents discomfort to the patient due to its smooth, rounded and tapered configuration.

To obtain an endometrial tissue sample, shaft 22 is extended through the passageway 34 of housing 20 further into the uterine cavity 16 until the second end 72 of tapered head portion 48 engages the end wall of the uterine cavity 16, as in FIG. 1. Again, the patient suffers little or no discomfort due to the rounded configuration of the second end 72 of head portion 48. Stop member 24 prevents the over-extension of shaft 22 and thus, prevents tapered head portion 48 from penetrating too deeply into the end wall of uterine cavity 16.

As shaft 22 is extended from housing 20, curved portion 46 of shaft 22 resiliently flexes to its original working configuration, as seen in FIGS. 2 and 3. Curved portion 46 thus assumes a shape within uterine cavity 16 which enhances contact of the tabs with the endometrial surface 18, as in FIG. 1. Shaft 22 is then rotated 360° in the first direction such that scraping tabs 60 penetrate the mucus of the endometrial surface 18 and disengage endometrial tissue cells. Tapered head portion 48 facilitates the rotation of shaft 22 by preventing any radial gyration of shaft 22. In other words, tapered head portion 48 provides a stabilizing effect to shaft 22 and prevents shaft 22 from swinging in a wide arc within uterine cavity 16. This helps to prevent any undesirable abrasions within the uterine cavity 16. As the scraping tabs 60 disengage the endometrial tissue cells, the cells become free floating from the endometrial surface 18.

As shaft 22 is rotated in the second direction opposite the first direction, the collecting tabs 62 collect the free floating cells scraped from the endometrial surface 18 by the scraping tabs 60 and secure the cells for collection so that no cell loss results when shaft 22 is urged into its storage position upon retraction within housing 20. The off-set nature of the tabs 60 and 62 prevents the scraping tabs 60 from scraping the cells collected by the collecting tabs 62. Also, the flexible nature of shaft 22 and the configuration of curved portion 46 are advantageous since a global or panoramic tissue sample is obtainable without having to repeat this procedure.

After the collecting tabs 62 collect the tissue sample, shaft 22 is retracted within passageway 34 of housing 20 until the first end 70 of head portion 48 engages the distal end 32 of housing 20 as in FIG. 4. Curved portion 46 again flexes inwardly toward longitudinal axis 40 and conforms to the diameter of passageway 34, thereby allowing easy retraction of shaft 22 within housing 20. Biopsy instrument 10 is then withdrawn from the uterine cavity 16 through the cervical opening 14 and out through the vaginal canal 12. The cell sample is safely maintained within housing 20 as biopsy instrument 10 is withdrawn from the patient. The cells are then available for testing.

It is to be understood that while certain forms of this invention have been illustrated and described, it is not limited thereto except insofar as such limitations are included in the following claims and allowable equivalents thereof.

Having thus described the invention, what is claimed as new and desired to be secured by Letters Patent is as follows:

1. A device for recovering tissue from an uterine cavity, comprising:
    an elongated housing having a distal end and proximal end and a passageway extending therethrough; and
    a single flexible shaft having a primary longitudinal axis and being receivable within said passageway, said shaft having a proximal end and distal end and a curved portion off-set from said longitudinal axis adjacent said distal end of said shaft;
    said curved portion having at least first and second tabs being longitudinally spaced apart and extending in opposed directions from said curved portion, said tabs generally positioned in an imaginary plane containing said longitudinal axis of said shaft with said first tabs scraping the adjacent tissue from the surface when said shaft is extended from within said passageway and rotated in a first direction within the uterine cavity, said second tabs securing the tissue scraped from the surface when said shaft is rotated in a second direction;
    a tapered tip portion at said distal end of said shaft thereof, said tip engaging a fundic surface of the uterine cavity for providing a pivot point for said rotations of said shaft.

2. A device as claimed in claim 1, wherein said tip portion is engageable with said distal end of said housing.

3. A device as claimed in claim 2, wherein said tip portion has a diameter greater than the diameter of said passageway where said tip portion is engageable with said housing.

4. A device as claimed in claim 1, wherein said tip portion has a rounded end.

5. A device as claimed in claim 1, further comprising a stop member coupled to said proximal end of said shaft engageable with said proximal end of said housing for delimiting the extension of said shaft from said passageway.

6. A device as claimed in claim 1, wherein said curved portion extends substantially parallel to said longitudinal axis.

7. A device as claimed in claim 1, wherein said housing is formed of rigid plastic.

8. A device as claimed in claim 1, wherein said curved portion of said shaft flexes toward said longitudinal axis of said shaft when in said passageway.

9. A device for recovering tissue from a surface forming an uterine cavity, comprising:
    an elongated housing having a distal end and proximal end and a passageway extending therethrough; and
    a single flexible shaft extendable and retractable through said passageway, said shaft having a proximal end and distal end, a tip portion at said distal end of said shaft and a distal curved portion off-set from a longitudinal axis of said shaft;
    said tip portion engageable with said distal end of said housing and tapering inwardly to form a tapered, rounded tip;
    said curved portion having first and second sets of tabs, said sets of tabs generally being in a plane containing a primary longitudinal axis of said shaft, said tab sets generally spaced apart and extending parallel to said longitudinal axis and alternately outwardly and inwardly from said curved portion so that said tab sets are not in alignment;
    said first set of tabs obtaining the tissue when said shaft is extended from within said passageway and rotated about said tip in a first direction, said second set of tabs securing the obtained tissue when said shaft is rotated about said tip in a second direction and retracted into said passageway.

10. A device as claimed in claim 9, further comprising a stop member coupled to said proximal end of said shaft, said stop member having a diameter greater than the diameter of said passageway and being engageable with said proximal end of said housing.

11. A device for recovering tissue from a surface forming an uterine cavity, comprising:
    an elongated housing having a distal end and proximal end and a passageway extending therethrough; and
    a single flexible shaft having a primary longitudinal axis and being receivable within said passageway, such shaft having a proximal end and distal end, a curved portion off-set from said longitudinal axis adjacent said distal end of said shaft, a working configuration which presents said curved portion of said shaft adjacent the tissue surface and a storage configuration which presents said curved portion flexed inwardly toward said longitudinal axis to allow said curved portion to withdraw into said housing;
    said curved portion having at least first and second tabs being longitudinally spaced apart and extending in opposed directions from said curved portion, said tabs generally positioned in an imaginary plane containing said longitudinal axis of said shaft with said first tabs scraping the adjacent tissue from the surface when said shaft is in its said working condition extended from within said passageway and rotated in a first direction within the cavity, said second tab securing the tissue scraped from the surface when said shaft is rotated in a second direction.

\* \* \* \* \*